(12) United States Patent
Nordell et al.

(10) Patent No.: US 12,031,166 B2
(45) Date of Patent: Jul. 9, 2024

(54) METHOD FOR THE PRODUCTION OF BIOGAS

(71) Applicant: Tekniska verken i Linköping AB (publ), Linköping (SE)

(72) Inventors: Erik Nordell, Linköping (SE); Sandra Waern, Linköping (SE); Jan Moestedt, Linköping (SE)

(73) Assignee: Tekniska verken i Linköping AB (publ), Linköping (SE)

( * ) Notice: Subject to any disclaimer, the term of this patent is extended or adjusted under 35 U.S.C. 154(b) by 145 days.

(21) Appl. No.: 17/614,106

(22) PCT Filed: May 27, 2020

(86) PCT No.: PCT/EP2020/064775
§ 371 (c)(1),
(2) Date: Nov. 24, 2021

(87) PCT Pub. No.: WO2020/239878
PCT Pub. Date: Dec. 3, 2020

(65) Prior Publication Data
US 2022/0307058 A1    Sep. 29, 2022

(30) Foreign Application Priority Data

May 28, 2019 (SE) .................................. 1950637-7
May 28, 2019 (SE) .................................. 2050149-0

(51) Int. Cl.
C12P 1/00     (2006.01)
C12M 1/107    (2006.01)
C12P 5/02     (2006.01)

(52) U.S. Cl.
CPC ...................................... *C12P 1/00* (2013.01)

(58) Field of Classification Search
CPC ............ C12P 1/00; C12P 5/023; C12M 21/04
See application file for complete search history.

(56) References Cited

U.S. PATENT DOCUMENTS

| 6,299,774 | B1 | 10/2001 | Ainsworth et al. |
| 8,613,894 | B2 | 12/2013 | Zhao et al. |
| 2007/0141691 | A1 | 6/2007 | Hirl |
| 2017/0088803 | A1 | 3/2017 | Knoop |
| 2018/0141841 | A1 | 5/2018 | Jardel et al. |

FOREIGN PATENT DOCUMENTS

| DE | 10336209 A1 | 3/2005 |
| DE | 102008056739 A1 | 5/2010 |
| DE | 102010015137 A1 | 10/2011 |
| EP | 1185384 A1 | 3/2002 |
| EP | 1365598 A2 | 11/2003 |
| EP | 3181524 A1 | 6/2017 |
| SE | 1150954 A1 | 4/2013 |
| WO | 0100341 A1 | 1/2001 |
| WO | 2004016796 A1 | 2/2004 |
| WO | 2012128558 A1 | 9/2012 |
| WO | 2014076483 A3 | 5/2014 |
| WO | 2014148565 A1 | 9/2014 |
| WO | 2016066752 A1 | 5/2016 |
| WO | 2017197508 A1 | 11/2017 |
| WO | 2020239878 A1 | 12/2020 |

OTHER PUBLICATIONS

International Search Report and Written Opinion for International Application No. PCT/EP2020/064775 dated Aug. 14, 2020, (20 pages).
Zhang et al., "Effect of inoculated and uninoculated aeration pre-treatment on nutrients and phytotoxicity of anaerobic digestion effluent," Scientific Reports, vol. 8, No. 1, 2008, (9 pages).
Javier et al., "Hydrocyclone as a cleaning device for anaerobic sludge digesters in a wastewater treatment plant," Journal of Cleaner Production, vol. 87, No. 4, pp. 550-557, 2015, (8 pages).
Verma, "Anaerobic Digestion of Biodegradable Organics in Municipal Solid Wastes," Submitted in partial fulfillment of the requirements for Master of Science Degree in Earth Resources Engineering, Columbia University, 2002, (56 pages).
Ahn et al., "Effects of Pre-aeration on the Anaerobic Digestion of Sewage Sludge," Environmental Engineering Research, vol. 19, No. 1, pp. 59-66, 2014, (8 pages).
Girotto et al., "Effect of Aeration Applied During Different Phases of Anaerobic Digestion," Waste Biomass Valor, vol. 9, pp. 161-174, 2018, (14 pages).
Hu et al., "Influence of recirculation of liquid fraction of the digestate (LFD) on maize stover anaerobic digestion," Biosystems Engineering, vol. 127, pp. 189-196, 2014, (8 pages).
Loughrin et al., "Aeration to Improve Biogas Production by Recalcitrant Feedstock," Environments, vol. 6, Issue 4, 2019, (10 pages).
Tornwall et al., "Post-treatment of biogas digestate—An evaluation of ammonium recovery, energy use and sanitation," Energy Procedia, vol. 142, pp. 957-963, 2017, (7 pages).
Zeb et al., "Recycling separated liquid-effluent to dilute feedstock in anaerobic digestion of dairy manure," Energy, vol. 119, pp. 1144-1151, 2017, (8 pages).
"Luftning av biogödsel for att reducera metanmissionerna—Avfall Sverige," Rapport 2016:14 ISSN 1103-4092, (32 pages). (English Language Summary on p. 7).
Senfter et al., "Identifikation der Einflussgrössen für die Auslegung eines Trennaparates zur selektiven Störstoffabscheidung bei der Vo-Vergärung von organischen Restoffen in Abwasserreinigungsanlagen," i:Österr Wasser- und Abfallw, vol. 69, pp. 378-387, 2017, (10 pages). (English Language Abstract on p. 1).

*Primary Examiner* — Satyendra K Singh
(74) *Attorney, Agent, or Firm* — Kagan Binder, PLLC

(57) ABSTRACT

A method for producing biogas in an anaerobic digestion chamber from an un-treated organic substrate, wherein said un-treated organic substrate has a dry matter of content of in the range of 20 to 90% of total solids, wherein the method comprises the steps of, pre-treatment of the un-treated organic substrate, to form a slurry having a dry matter content of in the range of 8 to 19.9% of total solids, feeding said slurry to a digestion chamber; digesting said slurry in the digestion chamber to produce biogas and a digestate, wherein in said pre-treatment step a mixture of a dilution fluid and a liquid digestate from said digestion chamber is used to dilute the un-treated organic substrate.

5 Claims, 9 Drawing Sheets

1. Pre-hydrolysis tank
2. Pasteurization tank
3. Digester
4. Aeration tank

● –Pre-hydrolysis reactor control
■ – Pre-hydrolysis reactor diluted with aerated digestate
♦ - Pre-hydrolysis reactor diluted with digestate ● –Pre-hydrolysis reactor control
■ – Pre-hydrolysis reactor diluted with aerated digestate
♦ - Pre-hydrolysis reactor diluted with digestate

METHOD FOR THE PRODUCTION OF BIOGAS

CROSS-REFERENCE TO RELATED APPLICATIONS

This application claims priority to International Application No. PCT/EP2020/064775, filed May 27, 2020 and titled "METHOD FOR THE PRODUCTION OF BIOGAS," which in turn claims priority from a Swedish Patent Application having serial number 1950637-7, filed May 28, 2019, and a Swedish Patent Application having serial number 2050149-0, filed May 28, 2019, all of which are incorporated herein by reference in their entireties.

TECHNICAL FIELD

The present document relates a method for production of biogas by adding a liquid digestate to the process.

BACKGROUND

When producing biogas, it is possible to use several different substrates, such as slaughterhouse waste, food waste collected at households, and industrial waste. Sweden has a national target to collect food waste from households and treat this material biologically to utilize both nutrients and energy as biogas. In practice, this means that food waste has to be anaerobically digested such that biogas is produced, and that the digestate is utilized as a bio-fertilizer, to return nitrogen and phosphorus to agricultural lands. The biogas production process thus closes the biological cycle of these nutrients.

One problem associated with food or organic waste from mainly households is that it may also contain different types of impurities, such as plastic, metal, glass and textiles. These impurities, including the plastic bags or containers used to collect and contain the organic waste, must be removed before the waste can be digested. This is done through a pre-treatment of the waste, usually performed in several steps, before a so called slurry is obtained, which forms the base material for the digestion process. The food or organic waste in a container or bag usually has a dry matter content of about 30-35% (i.e. 65-70% is water). After processing of the organic waste, the slurry usually has a dry matter content of around 8-19.9% (i.e. approximately 80.1-92% is water), which means that different types of fluids/liquids have been added to the waste. The addition of fluids is made to obtain a liquid slurry to achieve a slurry which can easily be pumped through the system since, if no liquids are added, the viscosity would be unreasonably high, which makes pumping and heat-exchanging difficult for the pasteurization step and the subsequent digestion chamber. Moreover, without addition of liquid, the separation of impurities is hard without simultaneously removing organic matter. Conventionally a dilution fluid made up of water (mainly freshwater/tap-water) and different types of diluted liquids, such as for instance washing water from the dairy industry, milk, or other such fluids, are used for this process.

However, mixing dilution liquids into the food waste increases the amount of bio-fertilizer, without increasing the actual amount of nutrients (such as phosphorus and nitrogen). This means that a loss of concentration of the nutrients occurs in this process. The bio-fertilizer is transported by closed lorries to the farmers, and the dilution thus leads to increased costs, in terms of water and transportation, and of course puts a load on the environment. Further to this, the retention time in the digestion chamber (i.e. the time that the material is in the chamber) is reduced and this leads to a decreased time for the slurry to be digested. There is therefore a need to reduce the impact on the environment, to increase the retention time in the digestion chamber, and increase the concentration of nutrients in the bio-fertilizer.

There are also other applications within pre-treatments such as mixing of substrates that requires a liquid such as water or other liquids. In order to digest products such as stillage, fat, grass silage, fodder or other organics, dilution with a liquid might be needed in order to achieve a pumpable slurry. The lower viscosity the dilution liquid has, the less liquid is required. Addition of a lot of water is not favorable since it dilutes the bio-fertilizer and shorten the hydraulic retention time in the digester.

Moreover, in some cases grit and gravel (heavy inert particles) need to be removed from a substrate such as processed food waste (slurry) or other pumpable waste. The most common way to remove inert particles from the substrate is by the use of a hydro-cyclone that amplifies the gravidity of the heavy particles, which then can be separated from the organic waste. The main disadvantages with this method is that the cyclone requires water to work. This is both costly as well as negative for the bio-fertilizer quality due to dilution. In addition it shortens the retention time of the substrate in the upcoming digester.

SUMMARY

It is an object of the present disclosure, to provide an improved method for producing biogas, and bio-fertilizers as well as an additive for dilution of substrate material used in the in the production of biogas.

The invention is defined by the appended independent claims. Embodiments are set forth in the appended dependent claims and in the following description and drawings.

According to a first aspect, there is provided a method for producing biogas in an anaerobic digestion chamber from an un-treated organic substrate, wherein said un-treated organic substrate has a dry matter of content of in the range of 20 to 90% of total solids, wherein the method comprises the steps of:

pre-treatment of the un-treated organic substrate, to form a slurry having a dry matter content of in the range of 8 to 19.9% of total solids, feeding said slurry to a digestion chamber;

digesting said slurry in the digestion chamber to produce biogas and a digestate, wherein in said pre-treatment step a mixture of a dilution fluid and a liquid digestate from said digestion chamber is used to dilute the un-treated organic substrate.

By "un-treated organic substrate" is meant a material which is delivered from a source, the organic material may comprise different types of waste, usually food waste from households, food waste from industries, food waste from stores, slaughterhouse waste or other types of industrially produced organic waste materials, such as fodder and silage. The organic substrate may also be different types of crops used for production of biogas. By "dilution fluid" is meant conventional dilution fluids used for biogas production, such as freshwater, washing fluids from the dairy industry etc. By "liquid digestate" is meant a material which is taken from the digestion chamber and brought back into the pre-treatment step. By "biogas" is meant a mixture of gases produced by the digestion of the organic substrate in the absence of oxygen. The biogases thus include primarily methane and carbon dioxide, and they are most often used for fuel or for conversion to heat or electricity. The digestate is the material which is left after the digestion process of the slurry containing the organic waste has been carried out.

The digestate is also considered as a bio-fertilizer, which is brought back to agricultural land, depending on the type of the organic waste used in the process.

By using a mixture of conventional dilution fluids and a liquid digestate the amount of bio-fertilizer is reduced, with an increased concentration of nutrients, such as nitrogen and phosphorus as additional effect. This reduces the transportation cost and increases the value of the bio-fertilizer (per volume unit). By replacing some of the conventional dilution fluids with liquid digestate the water consumption in the biogas production process can be reduced, which also has a positive impact on the environment. In addition to this, the retention time of the digestate is increased, which increases the degree of degradation of the slurry.

According to the first aspect, the liquid digestate may be either an unaerated or aerated liquid digestate.

According to the first aspect the liquid digestate may be an aerated digestate, wherein the method further comprises aerating said liquid digestate in an aeration chamber prior to the introduction into the pre-treatment step where the digestate is aerated with any one of the gases selected from air, oxygen and nitrogen with a flow in the range of 0.1 to 100 m³ gas/m³ liquid h.

According to the first aspect the liquid digestate is an aerated digestate and wherein the method comprises aerating said liquid digestate prior to the introduction into the pre-treatment step during a time period of at least 1 hour.

Preferably the retention time in the aeration chamber is longer than 1 hour, conventionally between 1 and 24 hours.

The viscosity of the aerated liquid digestate is decreased compared to untreated digestate during the aeration step as measured in cP.

By aerating the liquid digestate it has been found that the viscosity as defined in [cP] has been greatly reduced, compared to unaerated liquid digestate. This means that by using the aerated liquid digestate in the pre-treatment step, the viscosity of the organic waste, and the slurry formed, can be reduced, without decreasing the concentration of the nutrients in the digested slurry as much as when using conventional dilution liquids only. It has further been found that by aerating the liquid digestate to form the slurry undesired side effects in the pre-treatment step and also in subsequent storage and pasteurization steps, such as the formation of methane, hydrogen sulfide or other poisonous or explosive gases, can be greatly reduced or abolished. It has also been found that using an aerated liquid digestate gives no negative effects on the biogas production in total, i.e. the production is neither increased nor decreased.

It has been found that the decrease of total amount of bio-fertilizer may be up to around 20-25%, which means that the nutrients, such as ammonium nitrogen, is accumulated in the digestion chamber, resulting in an increase of the nutrients by around 20%.

According to one embodiment of the first aspect the liquid digestate replaces at least 5% of the dilution fluid compared to conventional methods, or at least 25% of dilution fluid, or at least 50% of dilution fluid.

According to a second aspect there is provided an additive for use in the method according to the first aspect, wherein said additive comprises an aerated liquid digestate from a digestion chamber.

The aerated liquid digestate has a viscosity as measured in cP which is lower than an untreated liquid digestate.

According to a third aspect there is provided a method of cleaning an un-treated organic waste substrate prior to introduction into a biogas production facility, wherein the cleaning is performed in a hydro-cyclone, and wherein said hydro-cyclone a cleaning liquid is used, wherein said cleaning liquid is at least partially composed of a liquid digestate from a digestion chamber.

According to the third aspect said liquid digestate may be either an unaerated or aerated liquid digestate. Preferably the liquid digestate is an aerated liquid digestate that has been treated in an aeration chamber.

Said aerated liquid digestate has a viscosity as measured in cP which is lower than an unaerated liquid digestate.

BRIEF DESCRIPTION OF THE DRAWINGS

Embodiments of the present solution will now be described, by way of example, with reference to the accompanying schematic drawings.

DESCRIPTION OF EMBODIMENTS

Figure 1:
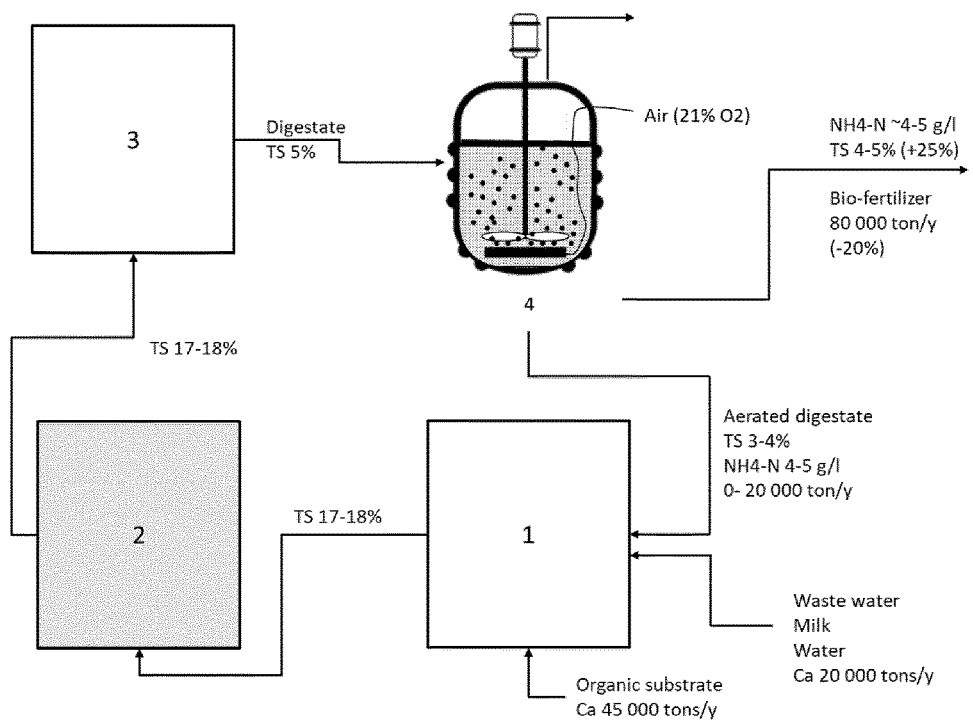
FIG. 1 is a schematic view of a biogas production process according to the inventive idea.

FIG. 1 illustrate an overview of the process. In a conventional biogas production organic waste material, such as food waste, industrial waste etc. is brought into a pre-treatment tank 1, here the waste material is pre-treated and thus mixed with dilution liquids, such as water (freshwater), or liquids from dairy or juice industry. In a facility such as the one at the Linköping municipal biogas plant about 45 000-50 000 metric tons of liquids are used annually. After the pre-treatment of the food waste, forming a slurry, the slurry usually has a dry substance content of 12-19.9%, i.e. a slurry material. The pre-treated waste is usually brought to a second step in the pre-treatment, which is at least one pasteurization chamber 1 or 2 or pre-hydrolysis chamber (storage tank for processed organic waste, slurry), wherein the pasteurization chamber 2 pathogenic microorganisms are reduced or killed. Here a certain degree of pre-hydrolysis occurs. After the pasteurization step the waste slurry material is brought to digestion chamber 3, where the waste slurry material is continuously digested under anaerobic conditions to form the gases called biogas, i.e. methane, carbon dioxide etc. The residue after digestion is called a digestate, and usually has a dry content of 3-9%. The digestate is used as a bio-fertilizer and is brought to the farmers in closed tanks, or to a treatment facility to increase the dry content. From a facility as the municipal biogas plant in Linköping, Sweden, approximately 80 000-120 000 metric tons of bio-fertilizer is produced annually, this bio-fertilizer usually has an ammonium nitrogen content of 3,000-4,000 mg/L. The farmer normally wants as high ammonium nitrogen and phosphorus content as possible. Also, the large volume of digestate to transport to the farmers is associated with a high cost.

According to one embodiment (not shown in the flow chart of the figures) of the invention a portion of the liquid digestate is brought from a digestion chamber 3 to the pre-treatment chamber 1 to replace some of the dilution liquids conventionally used in this pre-treatment step. By pre-treatment step is meant the step in the biogas process where the substrate material, i.e. undigested organic waste material of different origin is treated before it is brought to the digestion chamber.

A digestate from a digester chamber normally has a total solid (TS) content of 3-9% depending of the ingoing substrate and the degree of degradation of the material inside the digester. Moreover, the ammonium content varies depending of the substrate type, but if food waste is the main substrate the ammonium content typically is in the range of 2,000 to 4,000 mg/L (express as ammonium nitrogen).

According to an alternative embodiment of the inventive method a portion, or all, of the digestate is brought to an aeration chamber or tank 4. In the aeration chamber air is provided to flow through the digestate, thereby forming a liquid aerated digestate material. The liquid aerated digestate material has a lower dry content compared to the untreated digestate, normally in the range of 2-8% based on total solids. In FIG. 1 it is shown that all of the liquid digestate removed from the digestion chamber is brought to and aerated in the reaction chamber, however it is sufficient that only the portion needed to for dilution in the pre-treatment chamber is aerated.

The aeration may be performed, but not limited to, aeration with air, pure oxygen, and mixture of oxygen/nitrogen. In one embodiment the gas used in the reaction chamber comprises in the range of 1 to 100% $O_2$. Normally 21% of $O_2$ in air is used as the aeration gas. In one embodiment the flow of air in the reaction chamber is in the range of 0.1 to 100 $m^3$ gas/$m^3$ liquid and hour, more preferably 0.2 to 50 $m^3$ gas/$m^3$ liquid and hour and even more preferable 0.5 to 5 $m^3$ gas/$m^3$ liquid and hour.

According to one embodiment the retention time of the liquid digestate in the aeration chamber is in the range of 1 to 500 hours, more preferably 2 to 100 hours and even more preferable 12 to 48 hours. In one embodiment the retention time is at least 1 hours, or at least 2 hours.

According to this embodiment the viscosity of the aerated liquid digestate material has been reduced by at least 1%, more preferably by 10% and even more preferable by 25% compared to the untreated, i.e. not aerated liquid digestate material. This reduction of viscosity may be essential for the slurry produced in the pre-treatment step as it must have a certain viscosity for it to be fed in the system.

According to the invention around 50% of the dilution liquids can be replaced by the liquid digestate material, both untreated and treated. Preferably an aerated liquid digestate is used. A replacement of around 50% of the dilution liquids leads to a reduction of the total amount of bio-fertilizer by around 20-25% (under the conditions as set out in the municipal biogas facility in Linköping, Sweden). This results in an accumulation of ammonium nitrogen in the digestate chamber as well as in the bio-fertilizer, which in turn leads to an increase of ammonium nitrogen with about 20-25%. Thus, the water consumption decreases as well as the need for transportation of bio-fertilizer from the site to farmers land, thus providing a substantial economical saving. These amounts and improvements are all related to the specific conditions of the plant, and to the specific conditions of the raw material for the process.

Experimental Data

Trials have been performed in several different sets. The first trial set was aimed at simulating a semi-continuously fed storage tank for food waste, food waste and liquid digestate and food waste and aerate liquid digestate—naturally a pre-hydrolysis (controlled or uncontrolled) occurred when storing the slurry. In the tank a microbial culture was formed which could perform pre-hydrolysis of the slurry. The pre-hydrolysis reactors operated at a temperature of 55° C. In the second trial set both a pre-hydrolysis and a succeeding continuous biogas process for 275 days, i.e. a digestion chamber, were simulated.

In both trial sets a mixture matrix according to Table 1 were used.

TABLE 1

| | Food waste TS = 30% | Processed slurry of food waste and slaughterhouse waste TS = 15% | Tap water | Milk | Liquid untreated Digestate | Aerated liquid digestate | Total sum | Theoretic dry contents in the pre-hydrolysis reactor |
|---|---|---|---|---|---|---|---|---|
| Slurry | 57% | | 33% | 10% | | | 100% | 16.2% |
| Slurry with aerated liquid digestate | 57% | | 8% | 10% | | 25% | 100% | 17.3% |
| Slurry with liquid digestate | 57% | | 8% | 10% | 25% | | 100% | 17.2% |
| Slurry from day 180 in trail 2 | | 75% | 25% | | | | 100% | 11.0% |
| Slurry with aerated liquid digestate from day 180 in trail 2 | | 75% | | | | 25% | 100% | 12.3% |

Figure 2:
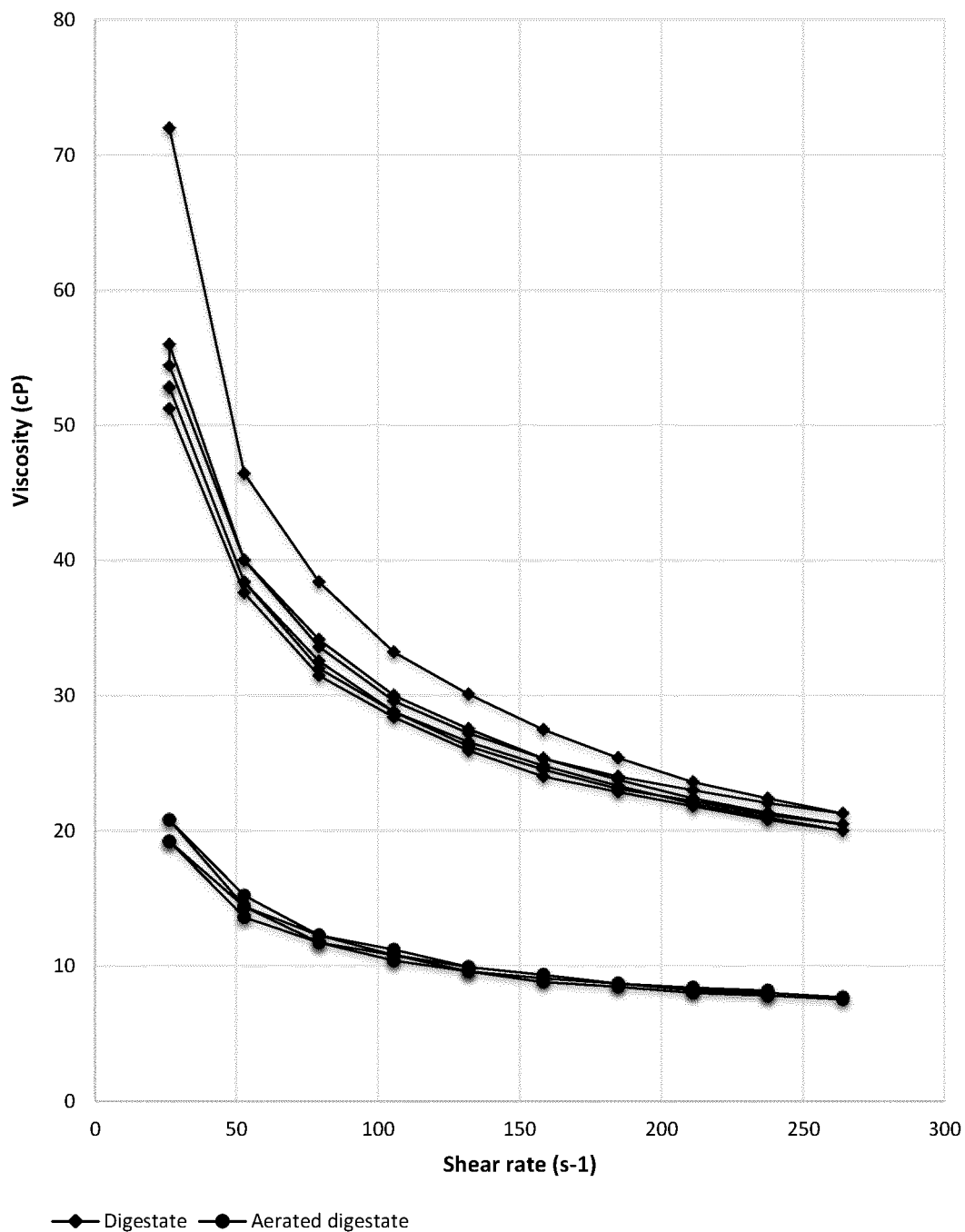
FIG. 2 is a graph showing the viscosity of aerated and unaerated digestate.

Before the trials were initiated the viscosity of the liquid (untreated) digestate and the aerated liquid digestate (air; 24 hours, 0.5 l O$_2$/l h; temperature 38° C.) was analyzed. These data showed that the viscosity was greatly reduced in the aerated liquid digestate, compared to the untreated liquid digestate. This surprisingly turned out to be an important effect of the aeration process, since the dilution liquid for the pre-treatment of the organic waste material, since the slurry that is formed needs a certain viscosity to be able to feed in the system. The results of the measurements are disclosed in FIG. 2. According to one embodiment the liquid digestate which is provided in the aeration chamber has a significantly lower viscosity than untreated digestate. At shear rate 50 (s$^{-1}$) in this example, the viscosity drops from 41 cP down to 14 cP, a decrease with 66% compared to untreated digestate.

Pre-Hydrolysis Reactor Trials

The trial showed that the concentration of ammonium nitrogen increased when liquid digestate was reintroduced instead of using water (alone) as dilution liquid. This is due to the fact that the liquid digestate contains approximately 3,000 mg ammonium/L and water 0 mg/L. Since the liquid digestate is to be continuously reintroduced into the digestion chamber, this will have effect on the concentration of the bio-fertilizer too.

The trial showed that a certain production of gases occurred, where the gas mainly comprised carbon dioxide, and some hydrogen gas, but only trace amount of methane. On the other hand, the introduction of untreated liquid digestate lead to the occurrence of a very high concentration of hydrogen sulfide, which could be problematic due to its corrosive, toxic and inhibitive effect on materials, people and the biogas process.

When using aerated liquid digestate the hydrogen sulfide concentration or level was very low, and also significantly lower in the comparative trial with food waste handled according to the conventional process (i.e. conventional dilution fluids). There are thus several advantages by using aerated digestate as liquid to mix and dilute the organic waste with.

Figure 3:
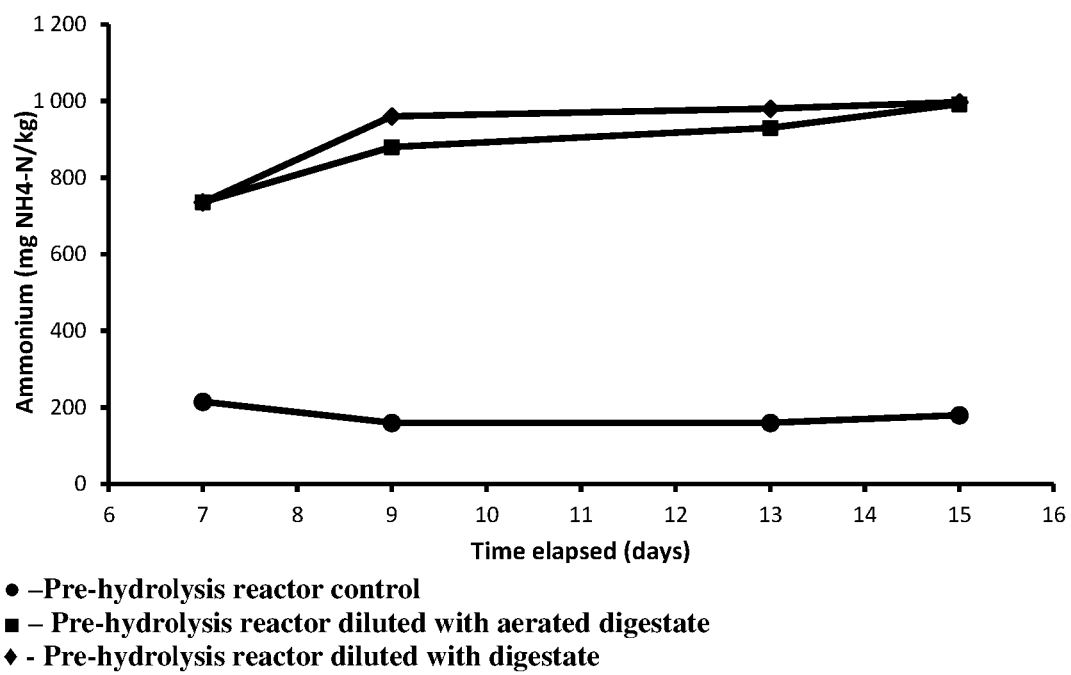
FIG. 3 is a graph showing a result of a pre-hydrolysis trial.
Figure 4:
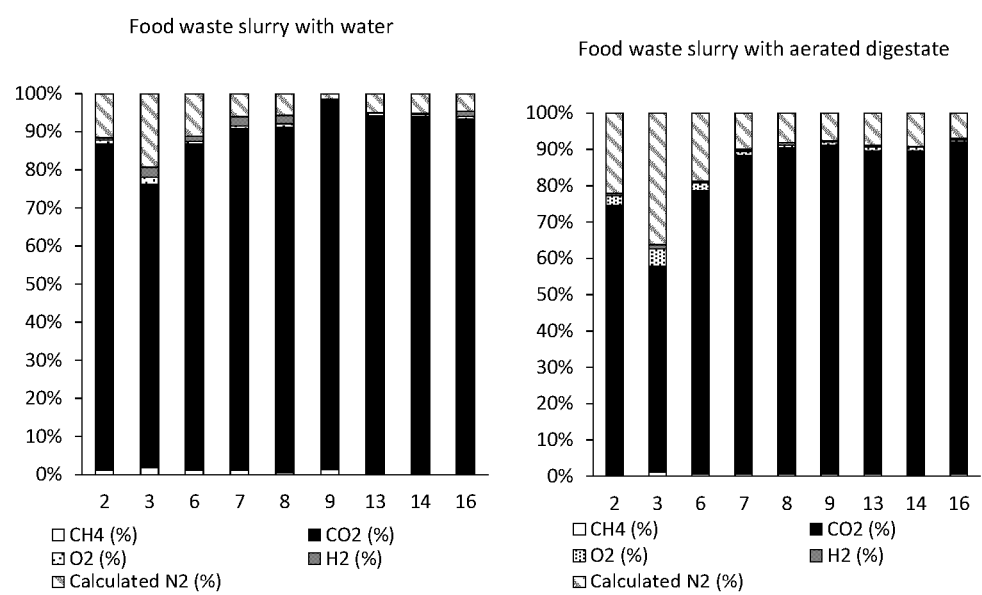
FIG. 4 is a graph showing a result of the gas composition from trials.
Figure 5:
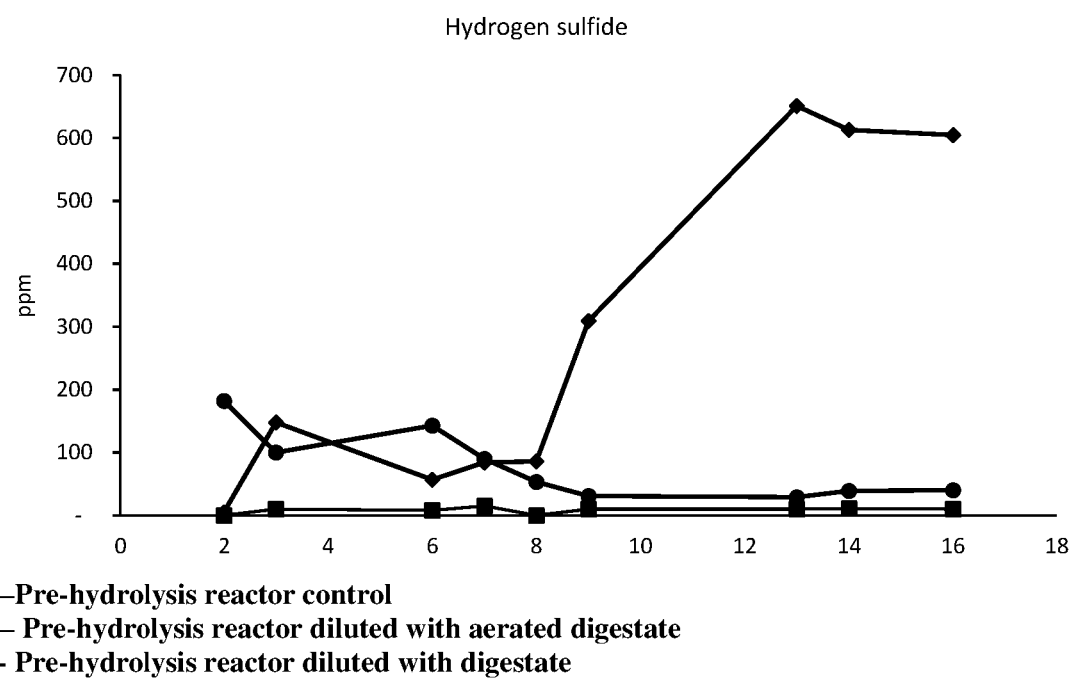
FIG. 5 is a graph showing hydrogen sulfide content in the off-gases from the pre-hydrolysis step (storage of slurry).

The trial results are shown in FIGS. 3 to 5.

Aeration of the liquid digestate leads to inhibition of the production of methane gases (which has been disclosed in the article https://www.avfallsverige.se/aktuellt/nyhetsarkiv/artikel/luftning-av-biogodsel-for-reducering-av-vaxthusgas-emissioner-etapp-2/).

Aeration of the liquid digestate results in a substantial decrease in viscosity of the liquid digestate.

Mixing an aerated liquid digestate with an organic waste such as food waste or food waste slurry does not lead to any side effects with regards to the production of methane gas in the pre-treatment step, hydrogen sulfide, or other toxic or explosive gases (such as hydrogen).

Mixing of both aerated and untreated liquid digestate increases the nitrogen concentration from approximately 200 mg/L to 1000 mg/L in a pre-hydrolysis process of food waste, which leads to decrease in the amount of bio-fertilizer, which in turn leads to decrease in transportation costs, increase of value of the bio-fertilizer (as calculate based om unit volume), reduced water use, and increased energy content in the slurry for digestion.

Continuous Trials

Figure 6:
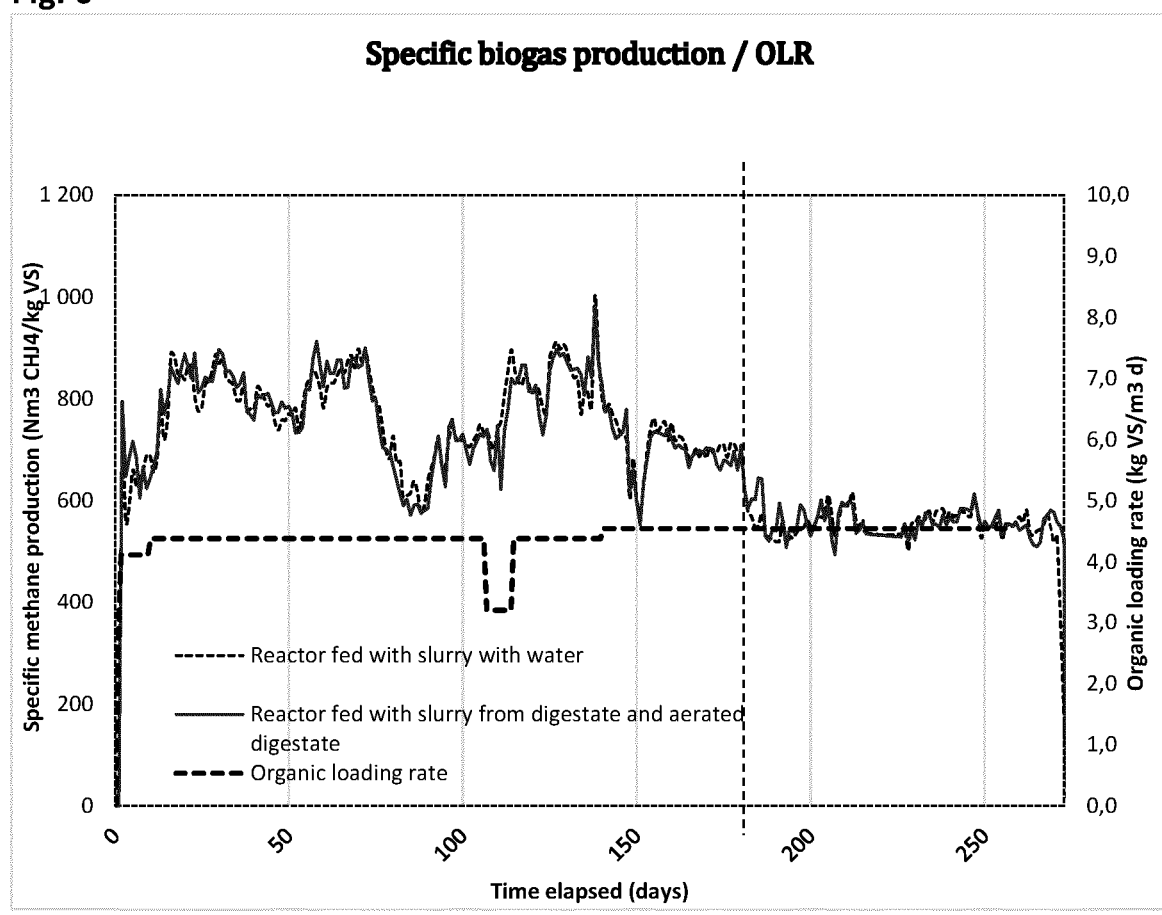
FIG. 6 is a graph showing the specific gas production in the continuous trail.

In the continuous trial (feed once every day) the purpose was to not only simulate the pre-hydrolysis, but also to feed the formed slurry to a continuous biogas production chamber. The experiment elapsed for 275 days. All reactors where inoculated at the start with digestate from the digesters at Linköping biogas plant (Sweden). The reactors used were specially adjusted for the purpose, all described in the patent by Nordell et al (Patent SE1150954 A1). The pre-hydrolysis reactors operated at a temperature of 60° C. The digesters were operated at a temperature of 42° C. As a model plant the municipal biogas production plant of Linköping, Sweden was used. In this plant a dominating amount of food waste is used as organic material, but also some slaughterhouse waste and other minor industrial waste fractions such as fat, stillage and alcohols. The retention time was determined to 35 days in the digestion step and three (3) days in the pre-hydrolysis step (storage tank), i.e. approximately the same as in the pre-hydrolysis trial. The organic loading rate in the digesters were 4.0-4.5 kg VS/m$^3$ day during the experiment. The first 30 days were used as start-up period were both reactors received the same slurry (food waste, milk, water). After that the experiment started and the pre-hydrolysis connected to the experiment reactor started to receive digestate in the amounts described in Table 1. After 180 days, the digestate re-circulation was replaced with aerated digestate, until day 275 when the experiment ended. When untreated digestate were used, fresh digestate from the experiment reactor were used to recirculate the same day. The aeration of the digestate from the experiment reactor took place once a week with an air flow of approximately 1 L O$_2$/L h, T=38 C and exposure time 24 h. To facilitate the trial, the gaseous phase from the pre-hydrolysis was continuously aerated and no gas production/composition was measured. The trial was designed this way since the focus was to examine the effect on the bio-fertilizer and the stability of the process in the digestion chamber. The pre-hydrolysis reactors were fed daily with a mixture of food waste, water, milk, digestate or aerated digestate (see Table 1). And subsequently the slurry from those were fed into the digesters, one digester fed with slurry formed from food waste, water and milk; and another reactor fed with slurry formed from food waste, digestate (or aerated digestate), water and milk. A comparative trial between using an untreated and aerated liquid digestate is provided in FIGS. 6 to 8.

Figure 7:
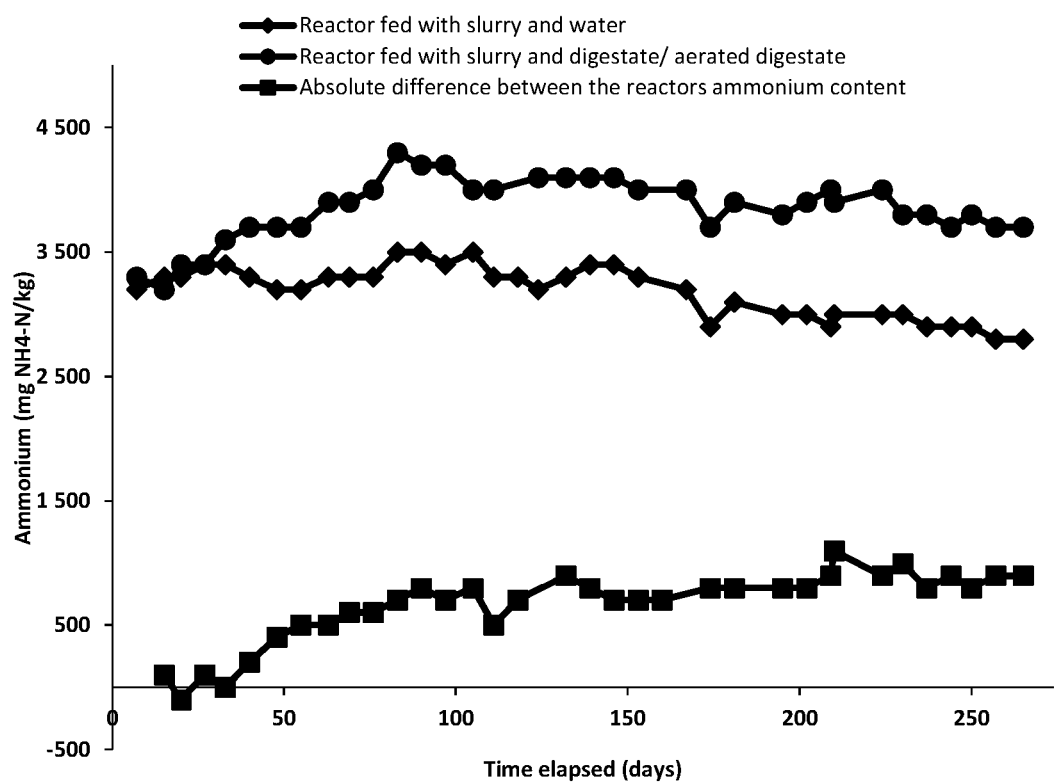
FIG. 7 is a graph showing the amount of ammonium nitrogen in the digestion chamber.

The trials verified that reintroducing both untreated and aerated liquid digestate results in an increase of the ammonium nitrogen content in the bio-fertilizer (and also the total nitrogen content), moreover, an up concentrations of all types of inert material, metals and mineral will of course appear in the same rate. FIG. 7. shows the ammonium nitrogen content of the digestate from the two digesters fed with different slurries. The reactor fed with slurry produced from the aerated digestate-mixture has a steady higher ammonium nitrogen content than the control. Moreover, at steady-state condition (3 retention times, or ~105 days from the start of recirculation of digestate, thus day 135) the increase in ammonium nitrogen is 800 mg/L. The rest of the experiment showed a steady increased value of ammonium with an average increase of 850 mg/L in the experiment reactor compared to the control reactor. This corresponds to an increase with about 28% compares to the ammonium nitrogen in the control reactor (FIG. 7). There were no negative effects on the production of biogas, i.e. the production was neither increased nor decreased.

Figure 8:
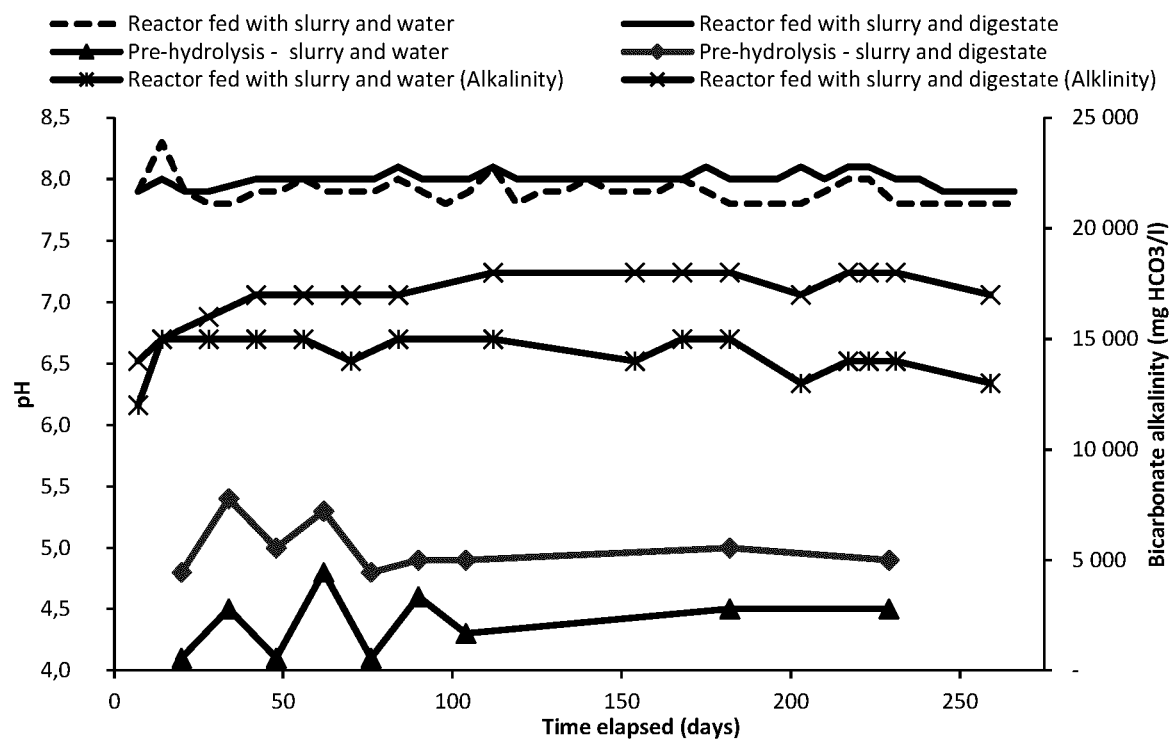
FIG. 8 is a graph showing pH and alkalinity.

Moreover, the replacement of water with aerated digestate (or digestate) results in a higher pH, 8.0, compared to 7.8 in the control reactor (FIG. 8). This is due to the increased amount of ammonium ions which force the pH up and potentially stress the biogas process. However, the volatile fatty acids concentration was low or below the detection limit during the whole trail in both reactors (data not shown).

Moreover, the increased amount of ammonium and carbonates results in a higher buffer capacity, which is desirable in a biogas process (FIG. 8).

Use of the Additive in Hydro-Cyclones to Replace Water

In some cases grit, gravel, glass etc. and heavy inert particles need to be removed from a substrate such as processed food waste (slurry) or another pumpable waste or material. The most common way to perform this is by use a hydro-cyclone that amplifies the gravidity of the heavy particles, which then can be separated from the organic waste.

EXAMPLE

At Linköping biogas plant (Linköping, Sweden) a cyclone is mounted in the circulation of the storage tank for processed food waste, the slurry. The slurry has a TS content of 14-16% in normal case. On an annual basis around 90 000 tons of slurry will pass the process. The cyclones use around 10-15 L water/min to work, resulting in 5,000 m$^3$ water per year in consumption. Thus, the dilution of the slurry is at this plant 5-6% due to the extra water added in this step, to separate heavy inert particles such as (but not limited to) grit and gravel from the organic slurry.

Figure 9:
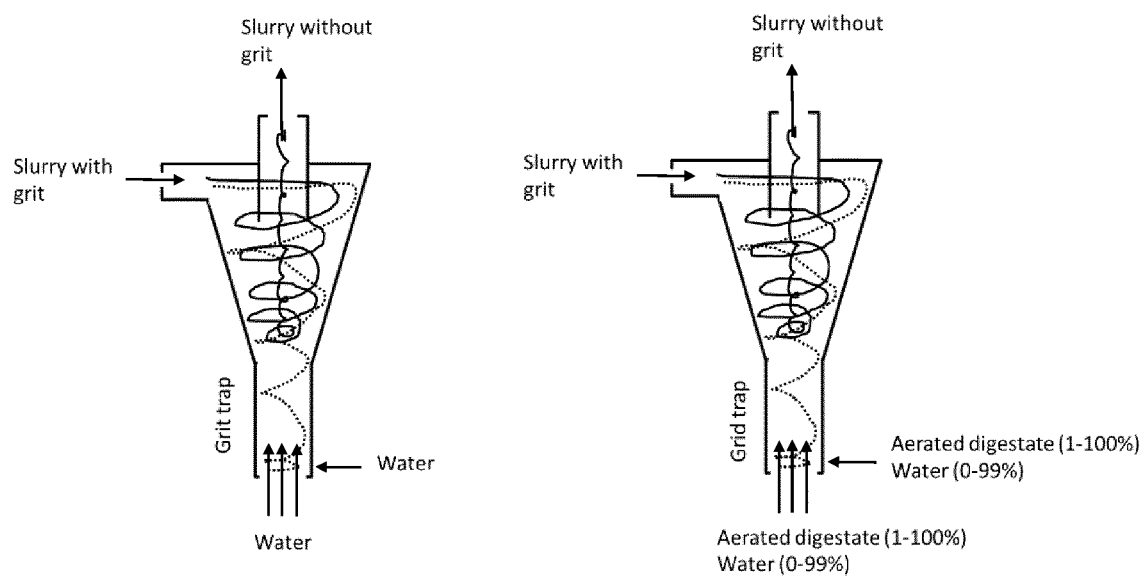
FIG. 9 is a graph showing the principle for the hydro-cyclone with water and/or aerated digestate as a liquid additive.

The high water consumption is both a cost and dilutes the bio-fertilizer as well as shortened the retention time of the substrate in the upcoming digester. By instead using aerated digestate (and thus a liquid with low viscosity), the water consumption may be cut with 1-100% compared to the common used technique with water. Moreover, since the aerated digestate is mixed-in to a substrate flow where the grit should be separated, there is of greatest importance to avoid gas bubbles and gas formation. Since the aerated digestate lacks dissolved methane and has low content of carbon dioxide this is a suitable liquid. Finally, the aerated digestate has a low viscosity, which is a requirement to be able to use the digestate as a counter flow in the cyclone. By using aerated digestate in the cyclone, dilution can be avoided as the aerated digestate contains high amount of nitrogen and phosphorus etc. which is desirable in the bio-fertilizer. Even more positively, this cuts the amount of transports needed to transport the bio-fertilizer to the farmers at the end of the process. See FIG. 9.

The invention claimed is:

1. A method for producing biogas and a digestate in an anaerobic digestion chamber from an un-treated organic substrate, wherein the un-treated organic substrate has a dry matter of content of in the range of 20 to 90% of total solids, wherein the method comprises the steps of:
    pre-treating the un-treated organic substrate to form a slurry having a dry matter content of in the range of 8 to 19.9% of total solids,
    feeding the slurry to the anaerobic digestion chamber, and
    digesting the slurry in the anaerobic digestion chamber to produce biogas and a digestate,
    wherein, in the pre-treatment step a mixture of a dilution fluid and a liquid digestate from the anaerobic digestion chamber is used to dilute the un-treated organic substrate,
    wherein the liquid digestate is an aerated liquid digestate,
    wherein the method comprises aerating the liquid digestate prior to the introduction into the pre-treatment step for a time period of at least 1 hour, and
    wherein the viscosity of the aerated liquid digestate measured in centipoise (cP) is reduced at least 10% compared to an unaerated liquid digestate.

2. The method as claimed in claim 1, wherein the method further comprises aerating the liquid digestate in an aeration chamber prior to the introduction into the pre-treatment step where the liquid digestate is aerated with one of the gases selected from the group consisting of air, oxygen, and a mixture of oxygen and nitrogen with a flow in the range of 0.1 to 100 m$^3$ gas/m$^3$ liquid hour.

3. The method as claimed in claim 1, wherein the aerated liquid digestate replaces at least 5% of the dilution fluid used in conventional pre-treatment methods.

4. The method as claimed in claim 1, wherein the aerated liquid digestate replaces at least 25% of the dilution fluid used in conventional pre-treatment methods.

5. The method as claimed in claim 1, wherein the aerated liquid digestate replaces at least 50% of the dilution fluid used in conventional pre-treatment methods.

* * * * *